US005357949A

United States Patent [19]

Bertheau et al.

[11] Patent Number: 5,357,949

[45] Date of Patent: Oct. 25, 1994

[54] BREATHING PROTECTION INSTALLATION FOR AIRCRAFT PASSENGERS

[75] Inventors: Fernand Bertheau, Plaisir; Gérard Silber, Chilly Mazarin, both of France

[73] Assignee: Eros G.I.E., Plaisir, France

[21] Appl. No.: 988,272

[22] Filed: Dec. 14, 1992

[30] Foreign Application Priority Data

Dec. 13, 1991 [FR] France ............................. 91 15526

[51] Int. Cl.[5] ...................... A61M 16/00; A62B 7/04; A62B 9/02; F16K 31/26

[52] U.S. Cl. ......................... 128/204.29; 128/204.18; 128/205.25; 128/205.24; 137/81.1

[58] Field of Search ...................... 128/204.18, 204.29, 128/205.13, 205.24, 206.24, 207.12, 201.28, 204.25, 205.25; 454/71, 238, 239, 255, 256, 340; 137/81.1, 114

[56] References Cited

U.S. PATENT DOCUMENTS

| | | | |
|---|---|---|---|
| 2,220,905 | 11/1940 | Johnson | 128/204.29 |
| 2,306,382 | 12/1942 | Fink et al. | 128/204.29 |
| 2,608,200 | 8/1952 | Stockman | 128/204.29 |
| 2,818,861 | 1/1958 | Russell | 128/206.24 |
| 3,981,300 | 9/1976 | Williams | 128/142 |
| 4,335,735 | 6/1982 | Cramer et al. | 128/204.29 |
| 4,651,728 | 3/1987 | Gupta et al. | 128/204.29 |
| 4,856,507 | 8/1989 | Ouillon et al. | 128/204.29 |

FOREIGN PATENT DOCUMENTS

| | | | |
|---|---|---|---|
| 1129831 | 11/1962 | Fed. Rep. of Germany . | |
| 2614207 | 10/1988 | France . | |
| 828362 | 2/1960 | United Kingdom . | |
| 865084 | 4/1961 | United Kingdom | 128/204.29 |
| 1207153 | 9/1970 | United Kingdom | 128/204.29 |

*Primary Examiner*—Kimberly L. Asher

*Attorney, Agent, or Firm*—Larson and Taylor

[57] ABSTRACT

An oxygen breathing apparatus for protection of aircraft passengers against aircraft depressurization has a pressurized oxygen storage and a distribution unit operated responsive to loss of pressurization at high altitude for feeding a pipe with pressurized oxygen from the storage. The passenger masks have a face cover which is formed with an inwardly directed circumferential flexible sealing lip and are each connected to the pipe by a flexible hose having a metering orifice. The distribution unit delivers pressurized oxygen under a pressure which increases up to a first value which is reached when loss of pressurization occurs immediately under a predetermined altitude (about 40,000 ft) and has a second value, of about two times the first value as long as the altitude exceeds the predetermined value. In a modification, the second pressure is delivered for a given period, typically about 3 mn.

7 Claims, 3 Drawing Sheets

BREATHING PROTECTION INSTALLATION FOR AIRCRAFT PASSENGERS

BACKGROUND OF THE INVENTION

The invention relates to installations for protecting aircraft passengers against the risks of cabin depressurization during flights at high altitude.

Conventional installations for protecting passengers comprise a store of oxygen connected to a distribution unit which, in the event of the cabin depressurizing at high altitude, feeds oxygen at a pressure that increases with altitude to a distribution main having passenger masks connected thereto via respective flexible hoses formed with metering orifices. One such installation is described in document GB-A-828 362.

A protection installation is used infrequently. It must be made up of components that are lightweight, simple, cheap to make, and unlikely to break down. At present, the masks used in such installations are generally constituted by a shell of semi-flexible material which is fed continuously through an economizer bag into which the hose opens out. The economizer bag is connected to the inside of the face cover via an intake non-return valve. The face cover has a breath-out non-return valve fixed thereto and rated to maintain a pressure inside the face cover that is slightly higher than the pressure of the ambient atmosphere. While the user is breathing out, the intake valve is closed and the economizer or rebreather bag serves to collect the flow of oxygen provided by the source instead of allowing it to escape to the atmosphere.

The pressure of oxygen delivered by the distribution unit is selected as a function of the cross-sectional flow area of the metering orifices so as to provide the masks with a mean flow of oxygen that is sufficient to maintain the minimum oxygen partial pressure in the trachea as required by administrative regulations, and at any altitude.

That solution gives results that are acceptable up to altitudes of about 12 200 m. At higher altitudes, the present solutions do not provide effective protection against hypoxia. Unfortunately, airliners and business aircrafts are nowadays flying more and more frequently at altitudes exceeding 12 200 m, once they have lost weight due to consumption of part of their fuel.

At first sight, it would seem that satisfactory protection would require replacement of conventional installations of the type defined above with installations that include, for each mask, a demand regulator and a balanced breath-out valve (i.e. a valve that is insensitive to variations in downstream pressure), thereby enabling passengers to breathe pressurized pure oxygen by avoiding opening of the breath-out valve as soon as a determined pressure difference above ambient is reached. In practice, the cost and the complexity of such a solution would be prohibitive.

SUMMARY OF THE INVENTION

The present invention is intended to provide an installation that ensures acceptable protection up to altitudes of about 13 700 meters while only requiring limited modifications only to existing installations.

The invention is based on the observation that, in fact, present installations do not allow the wearer of a mask to breathe pure oxygen. During inhalation peaks, the mean oxygen flow rate and the volume of oxygen from the economizer bag are insufficient to prevent the pressure inside the mask from becoming slightly less than ambient, and that causes dilution air to enter via the anti-suffocation valve provided on the mask and via leakage between the face cover and the skin. The mean flow provided through the throttle does not satisfy the needs of certain passengers and/or is insufficient for ensuring pulmonary ventilation during periods of agitation. Unfortunately, it is not possible to overdimension the valve diaphragm or to increase the oxygen feed pressure under all circumstances since that would lead to oxygen being wasted and would require an oxygen storage of considerably greater weight and volume.

To solve the problem, there is provided an installation wherein the distribution unit is designed, in the event of depressurization, to supply oxygen to the distribution main at a predetermined pressure p1, either temporarily or as long as a pressure lower than the atmospheric pressure above a predetermined altitude (of about 12 200 m) is present, p1 being about twice the pressure p2 supplied immediately below the predetermined altitude, and in that each mask includes a shaped face cover having a flexible sealing lip and a non-balanced breath-out valve.

When the store and the distribution unit constitute a generator which generates oxygen by chemical reaction, the generator may merely be designed to first deliver a flow of oxygen at at least twice the rate delivered subsequently, for a period of time that is long enough to enable the crew to bring the aircraft down to an altitude of less than 12 200 meters, e.g. for a period of about 3 minutes: these circumstances often apply to an installation designed for a business aircraft.

By using this disposition, the additional capacity required of the store is only that required for protecting the passengers against hypoxia during the time it takes the crew to bring the aircraft down to a safe altitude.

In airliners, mask presentation boxes are interposed between the distribution unit and branch pipes. Each box contains breathing masks and is provided with a lock enabling the masks to be released so that they fall down in front of the passengers in the event of depressurization. In an advantageous embodiment of the invention, the distribution unit may be designed to feed the mask boxes at a high pressure p1 greater than the pressure p2 to be delivered upstream from the metering orifices each feeding one of the masks at altitudes of immediately less than 12 200 meters, in which case each mask box is provided with an altimeter-type pressure reducing valve situated upstream from the metering orifices together with means for by-passing the pressure reducing valve in response to receiving oxygen at the high pressure p1 from the distribution unit.

Feeding oxygen under pressure p1 does not significantly increase the relative pressure in the mask since that is limited by the breath-out valve. However, it does give rise to a significant increase in flow rate, thereby avoiding dilution of the oxygen by air ingress from the outside, thus guaranteeing that practically pure oxygen is breathed.

Such a box replaces some of the functions that are normally provided by the distribution unit in conventional installations.

The invention will be better understood from the following description of particular embodiments given as non-limiting examples. The description refers to the accompanying drawings.

DESCRIPTION OF EMBODIMENTS

Figure 1:
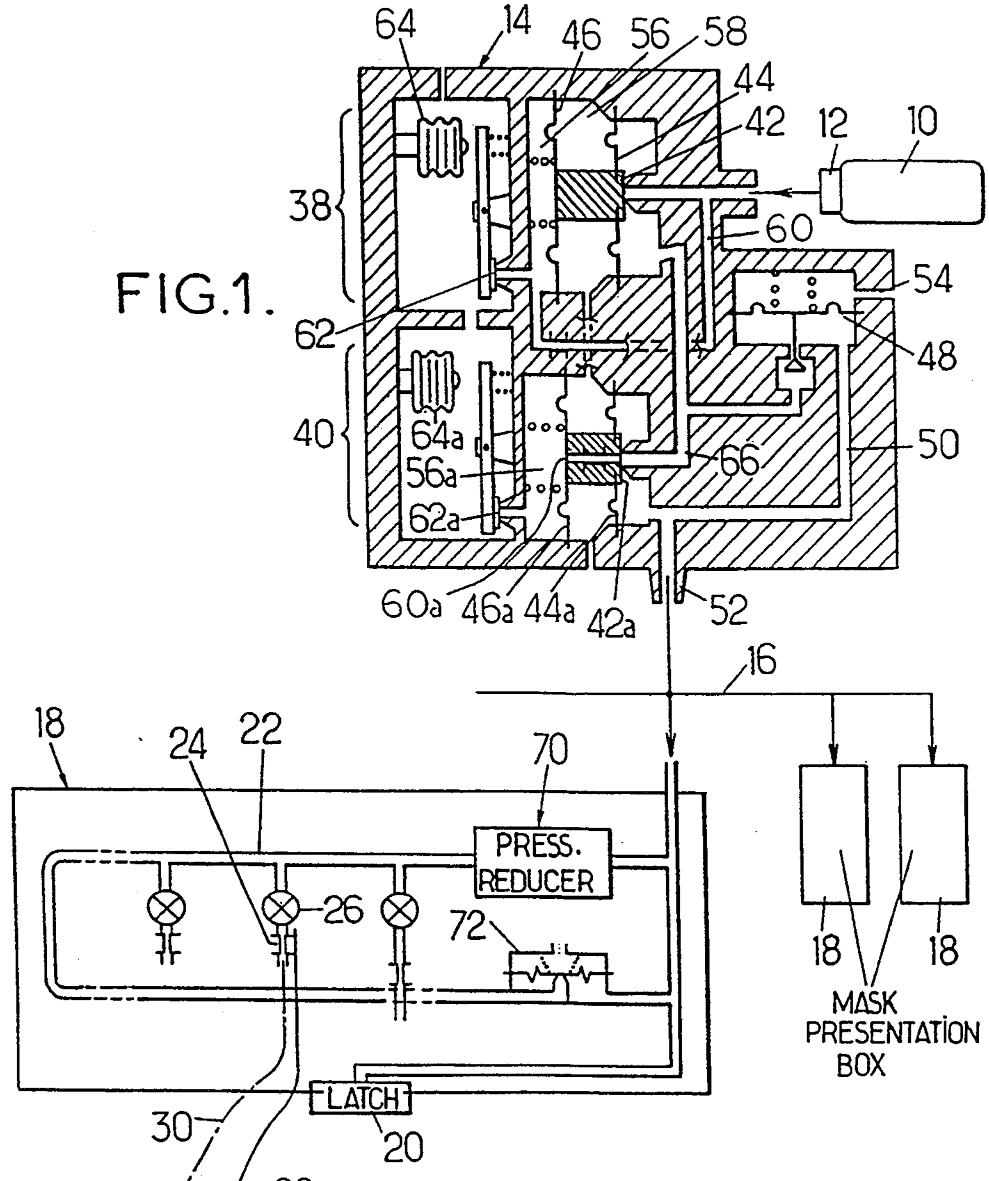
FIG. 1 is a theoretical diagram of an installation according to the invention, with only one of the mask boxes and only one mask being shown in full.
Figure 1:
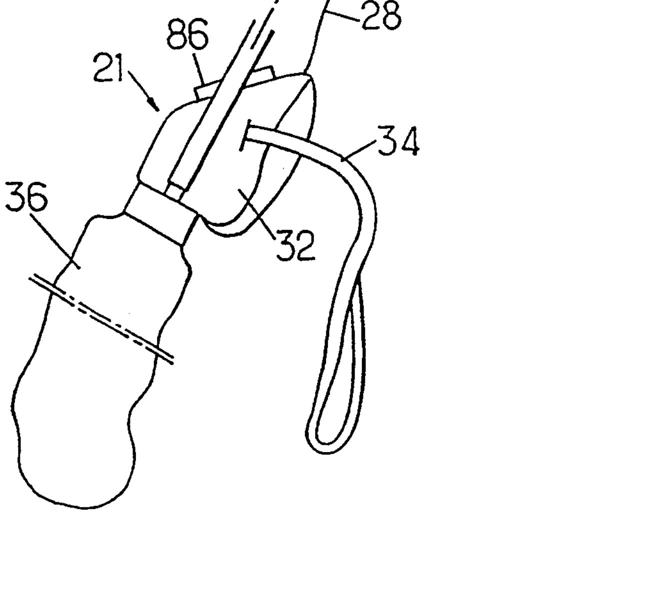

The installation shown diagrammatically in FIG. 1 is particularly suitable for use in a passenger airliner. This installation includes a store of pressurized oxygen 10 provided with a pressure reducing valve 12 that delivers oxygen at a pressure of 5 to 6 bars to a distribution unit 14. The distribution unit in turn feeds a general main 16 onto which mask boxes 18 are connected, with only one such box being shown in detail. The boxes are disposed over the rows of seats, and each is designed to release the masks 21 it contains in the event of depressurization. For this purpose, the bottom of the box 18 may constitute a lid provided with a latch 20 which is released in response to a pressure peak in the main 16 that is greater than a determined value p0. Unlocking may be achieved in some other manner, or the masks may be continuously available to passengers permanently, e.g. in business aircrafts.

Each box 18 includes a branch pipe 22 and each of the masks is connected thereto via a flow limiting metering orifice or restriction 24. In the example shown in FIG. 1, a shut-off valve 26 is located between the branch pipe and each of the masks 21, in series with the corresponding restriction 24. The shut-off valve is designed to be opened by the passenger pulling on a strap 28 which runs parallel to the flexible hose 30 connected to the mask 21.

The mask itself comprises a face cover 32 fitted with a resilient harness 34 for attaching the mask to the head, and with a flexible economizer bag 36.

The general disposition described above is conventional. However, in accordance with the invention, the distribution unit 14, the mask boxes 18, and the masks 21, are of special construction.

The distribution unit 14 is designed to feed the general main 16 with oxygen at a pressure that varies responsive to the pressure in the cabin, i.e. with "cabin altitude", in accordance with laws which depend on whether said altitude is lesser than or greater than 12 200 meters, i.e. 40 000 feet. As explained above, when the altitude exceeds 12 200 meters, even slightly, then the unit 14 supplies oxygen at a pressure p1 which is practically twice the pressure p2 at which it delivers oxygen when the altitude is hardly below 12 200 meters.

The distribution unit 14 shown in FIG. 1 is made in such a manner as not only to achieve this result, but also to deliver a short pressure pulse immediately after it detects depressurization to a cabin altitude above 3800 m (12 500 feet), for the purpose of opening the latches 20 of boxes 18. Numerous other structures are possible for the unit 14, pneumatically or electronically controlled responsive to signals provided by pressure sensors.

The unit 14 as shown includes a housing having an inlet connected to the pressurized oxygen storage 10 and an outlet connected to the distribution main 16. It may be considered as having two stages 38 and 40 of similar structure.

The first stage 38 includes a valve closure member 42 fixed to two diaphragms 44 and 46 and cooperating with a seat that surrounds the intake of oxygen from storage 10. The valve closure member 42 thus controls communication between the storage and a pressure reducing valve 48 of conventional structure which is connected by a passage 50 to the outlet 52. The pressure reducing valve 48 maintains the pressure at the outlet 52 constant relative to ambient pressure admitted via an orifice 54 as long as the second stage 40 does not intervene. The pressure action areas on the two diaphragms 44 and 46 are different. They define a chamber 58 which is connected to ambient air and they are subjected to the force of a spring which biases the valve closure member 42 toward its seat.

The larger area diaphragm 46 is subjected to the pressure difference between the chamber 58 and a chamber 56 connected to the intake via a restricted passage 60. The dimensions of the valve closure member 42 and of the diaphragms are such that the valve member opens whenever the chamber 56 is scavenged, i.e. whenever cabin altitude reaches 3800 meters.

The structure of the second stage 40 is similar to that of the first. The chamber **56*a* defined by the housing and the large area diaphragm 46*a* is connected to the valve having closure member 42*a* by a restriction 60*a*. The areas of the diaphragms 44*a* and 46*a* are selected so that the valve closure member 42*a* of the second stage opens as soon as the chamber 56*a*** is scavenged, i.e. when the cabin altitude reaches 12,200 meters.

As shown, the distribution unit 14 is designed to deliver, at its outlet 52, oxygen at the intake pressure thereof for a short period of time (long enough to open the latches of the boxes 18) if the pressure in the cabin falls below that corresponding to an altitude greater than 12,500 feet.

Operation is then as follows:

So long as cabin altitude remains below 12,500 feet (about 3800 meters) the valve closure member 42 remains closed by the pressure in the chamber 56. This chamber is at the outlet pressure from the pressure reducing valve 12 since a valve 62 remains closed.

In the event of depressurization above 12,500 feet, the capsule 64 opens valve 62. The chamber 56 empties. The valve closure member 52 opens. Oxygen from the pressure reducing valve feeds the second stage via a passage 66. The pressure forces exerted on the valve member **42*a* formed with a throttled passage 60*a* lift the valve closure member 42*a* and the pressure delivered by the pressure reducing valve 12 is transmitted directly to the outlet 52**.

So long as cabin altitude remains below 4000 feet (about 12,200 meters), the capsule **64*a* does not open the valve 62*a* of the second stage. In a few seconds, the chamber 56*a* fills with oxygen coming from the first stage via the throttle 60*a*. The direction in which the pressure forces act reverses and the valve closure member 42***a* closes again.

If on the other hand the cabin altitude exceeds 40,000 feet, the capsule 64*a* opens the valve 62*a*. The chamber 56*a* empties and the valve closure member 42*a* remains open. The pressure provided by the pressure reducing valve 12 is transmitted directly to the outlet 52.

Figure 5:
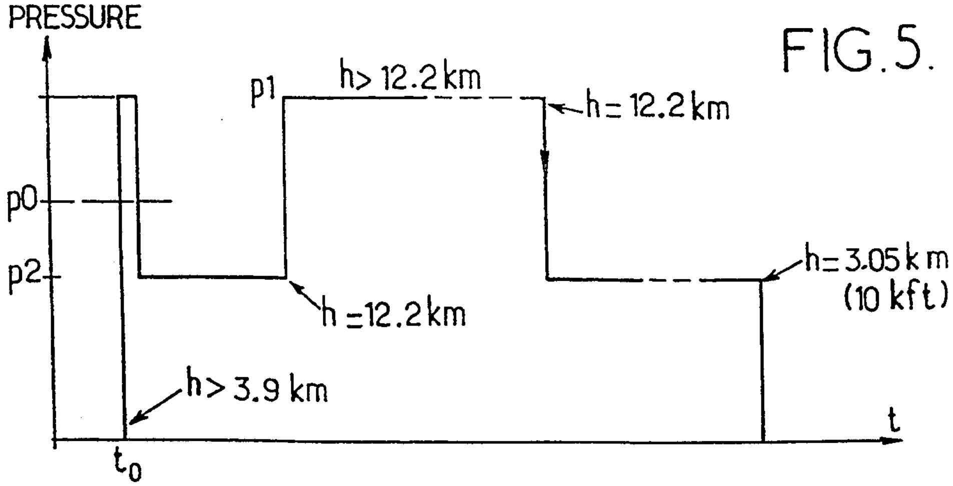
FIG. 5 is a graph showing, by way of example, a relationship between the pressure at the outlet of the distribution unit as a function of time for a particular hypothetical descent profile.

FIG. 5 shows a sequence corresponding to slow decompression during which the cabin altitude exceeds 12,200 meters, and then progressively returns to ground level. At instant t0, the pressure p1 at the outlet of the pressure reducing valve is applied to the boxes 18 to open the latches 20 which are designed to be tripped whenever pressure p0 is less than p1. The pressure then falls to a value p2, after which it rises to p1 again when an altitude of 40,000 feet is reached. Once the aircraft has descended below 40,000 feet, the pressure drops again to p2 and this continues until an altitude which is generally lower than 12,500 feet, and which is 10,000 feet, for example (about 3100 meters).

In each of the boxes 18, the branch pipe 22 is fed via a pressure reducing valve 70 when the applied pressure is equal to p2, and via a by-pass valve 72 when the applied pressure is equal to p1. The by-pass or short-circuit valve 72 may be constituted by a simple diaphragm urged towards a closed position against a seat by the pressure that prevails in the cabin and by the force of a spring and urged in the opposite direction by the force exerted on its central portion by the pressure that exists in the branch pipe 22, and at its periphery by the force exerted by the pressure at the inlet to the box 18. The diaphragm and the spring are such that the by-pass valve 72 opens when the pressure exceeds a predetermined value lying between p2 and p1.

Figure 2:
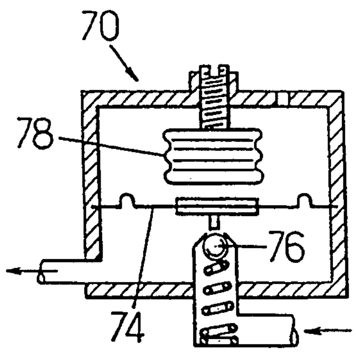
FIG. 2 is a diagrammatic representation of an altitude responsive pressure reducing valve suitable for use in a box of the kind shown in FIG. 1.
Figure 4:
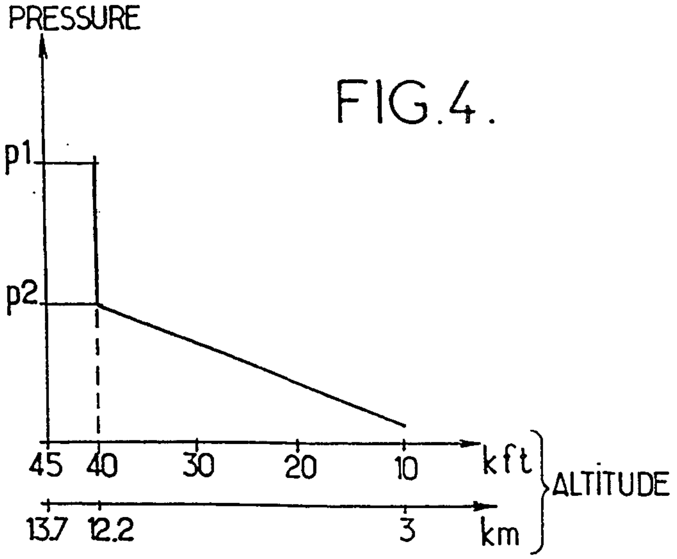
FIG. 4 is a graph showing a curve which represents a possible variation of pressure responsive to altitude, suitable for implementing the invention.

The pressure reducing valve 70 may be as shown in FIG. 2, for example and comprises a diaphragm 74 provided with a push-rod for opening a ball valve 76 and a capsule 78 designed to bear directly or via a spring on the diaphragm when the altitude in the cabin exceeds 10,000 feet. The pressure in the branch pipe 22 then varies responsive to cabin altitude in accordance with a relationship of the kind shown in FIG. 4.

As mentioned above, obtaining satisfactory protection implies that air leaks into the mask from the atmosphere be avoided.

To achieve this result, the face cover 32 of the mask 21 (FIG. 3) includes an inner lip 80 of flexible elastomer that defines a generally triangular opening that is shaped so as to be pressed against the bridge of the nose and the face by the internal pressure. The mask shown in FIG. 3 includes a valve block 82 which incorporates a flexible valve closure member 84 controlling admission from the economizer bag 36 along arrows f0. If the bag is empty, the assembly constituted by the flexible valve member 84 and the housing supporting it, can move upwardly as a whole to open a passage for additional air along arrows f1.

Figure 3:
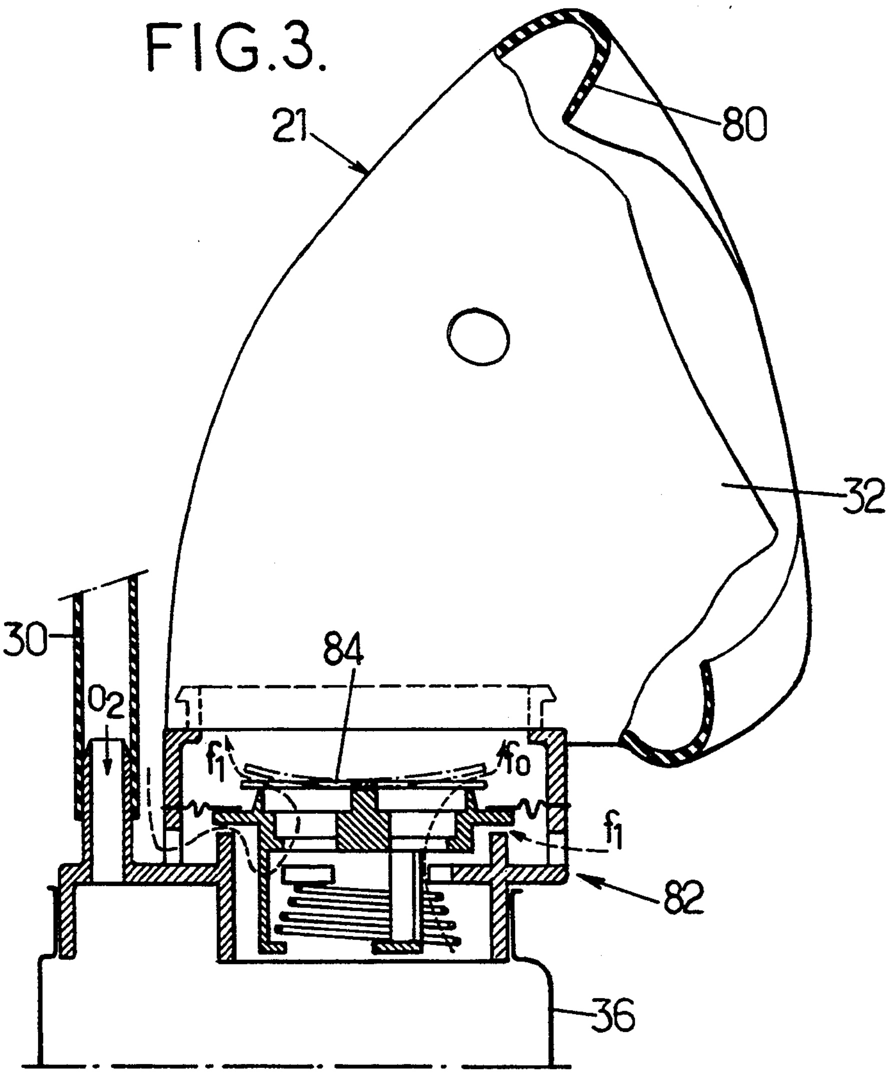
FIG. 3 is a diagram, in cross-section along the non-return valve axis, showing the principles of a connection between the face cover and the economizer bag of a mask suitable for use in the installation of FIG. 1.

The economizer bag 36 may be fed from a flexible hose 30 shown in FIG. 3 as being in front of the face cover, although it is normally placed on the side in practice, as shown diagrammatically in FIG. 1.

Breathing out may take place, for example, through an additional valve 86 which is calibrated by a spring, shown diagrammatically in FIG. 1, or through an annular breath-out valve (not shown) located at the periphery of the block 82 and having a flexible valve closure member whose stiffness determines the maximum relative pressure inside the mask.

Figure 6:
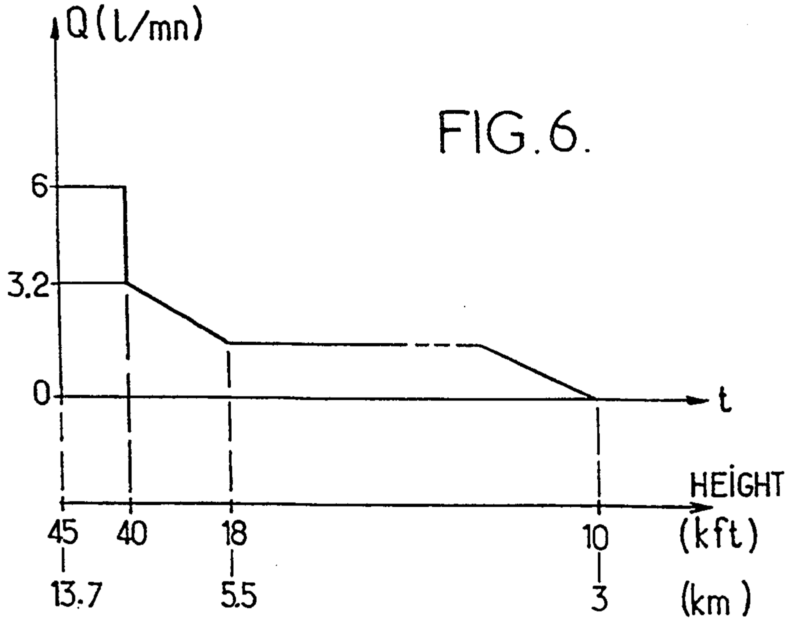
FIG. 6 is a graph showing a flow rate variationship suitable in a chemical generator.

If each mask is fed individually by a chemical generator, then the generator is designed, once triggered, to provide oxygen at a flow rate that varies in compliance with a relationship of the kind shown in FIG. 6, enabling oxygen to be supplied under the most critical conditions during descent from an altitude that generally cannot exceed 45,000 feet, i.e. 13,700 meters. Under such circumstances, the relationship obtained by adopting a variable composition or an "oxygen supply candle" of varying section can be of the kind shown in FIG. 6. It is designed to provide a flow rate of about 6 liters per minute (under conditions of normal temperature and pressure) for a period of time that is sufficient to enable the aircraft to be brought down from its maximum altitude of 13,700 meters to 12,200 meters, for example, after which the oxygen flow rate is reduced progressively while still being maintained for a period of time that is sufficient to allow the aircraft to be stabilized at an intermediate altitude, e.g. 18,000 feet (5,500 meters) prior to being brought down to a safe altitude of 10,000 feet (3,050 meters). In practice, it is generally satisfactory if oxygen is provided at the maximum flow rate for a period of about 3 minutes.

We claim:

1. An emergency oxygen breathing apparatus, said apparatus having means for protecting aircraft passengers from hypoxia at an altitude of up to 13,700 meters, upon aircraft depressurization, comprising: an oxygen storage unit; a distribution unit having an inlet connected to said oxygen storage unit and an outlet, said distribution unit being actuated in response to aircraft depressurization at high altitudes and delivering oxygen through said outlet at pressures which increase with altitude; pipe means for connecting to said outlet; a plurality of passenger masks each having a face cover formed with a circumferential inner flexible sealing lip and connected to said pipe means by a flexible hose having a metering orifice, said distribution unit having means responsive to cabin altitude for delivering oxygen to said pipe means under a pressure which (a) steadily increases with altitude up to a first predetermined value at a predetermined altitude, (b) abruptly increases to a second predetermined value which is of about two times the first predetermined value as soon as the altitude exceeds said predetermined altitude, and (c) remains constant at said second predetermined value of pressure as long as the altitude exceeds said predetermined altitude.

2. Apparatus according to claim 1, wherein each said mask is connected to said pipe means and to a flexible economizer bag via an inlet valve.

3. Apparatus according to claim 1, wherein each said mask has a non-compensated exhalation valve opening to the aircraft atmosphere.

4. An emergency oxygen breathing apparatus, said apparatus having means for protecting aircraft passengers from hypoxia at an altitude of up to 13,700 meters, upon aircraft depressurisation of a cabin accomodating said passengers, comprising:

an oxygen storage unit;

a distribution unit having an inlet connected to said oxygen storage unit, an outlet, a plurality of passenger masks, and pipe means for connecting said outlet to said plurality of masks, said distribution unit having means responsive to cabin pressure for delivering oxygen from said oxygen storage unit to said pipe means under a pressure which (a) steadily increases up to a first predetermined value as the cabin pressure decreases from an atmospheric pressure prevailing at a respiratory safe altitude, to a second value which is an atmospheric pressure prevailing at a predetermined altitude, and (b) abruptly increases to a second predetermined value, which is about constant and twice the first predetermined value, as soon as the cabin pressure decreases to lower than the atmospheric pressure at said predetermined altitude, and (c) remains constant at said second predetermined value as long as the atmospheric pressure remains below that found at said predetermined altitude; and said plurality of passenger masks each having a face cover formed with a circumferential inner flexible sealing lip and connected to said pipe means by a flexible hose having a metering orifice and having a non-balanced breath-out valve opening to the cabin atmosphere.

5. An emergency oxygen breathing apparatus, said apparatus having means for protecting aircraft passengers from hypoxia at an altitude of up to 13,700 meters, upon aircraft depressurization, comprising:

an oxygen storage unit;

a distribution unit having an inlet connected to said oxygen storage unit and an outlet, said distribution unit being actuated in response to aircraft depressurization at high altitude and delivering oxygen through said outlet at pressures which increase with altitude, said distribution unit having means responsive to cabin altitude for delivering oxygen to said outlet at a pressure which (a) steadily increases with altitude up to a first predetermined value which is attained at a first predetermined altitude, (b) abruptly increases to a second predetermined value at a second predetermined altitude which second predetermined value is about twice the first predetermined value, and (c) remains constant at said second predetermined value of pressure as long as the aircraft altitude exceeds said second predetermined altitude;

a plurality of mask presentation boxes, each box having an input connected to said outlet of said distribution unit and having an output connected to a plurality of pipes, each box further having a pressure reducing valve responsive to ambient aircraft pressure and means for by-passing said pressure reducing valve responsive to delivery of said second predetermined pressure at the outlet of said distribution unit; and a plurality of passenger masks each having a face cover formed with a circumferential inner-flexible sealing lip, each mask connected to one of said plurality of pipes by a flexible hose having a metering orifice.

6. Apparatus according to claim 5, wherein said first predetermined altitude is of about 12,200 meters.

7. Apparatus according to claim 5, wherein said distribution unit comprises:

a first valve stage responsive to ambient pressure having an inlet in continuous communication with said storage unit and an outlet, constructed to open as soon as the ambient pressure is lower than that corresponding to the second predetermined altitude, lower than said first predetermined altitude;

a pressure reducing valve responsive to ambient pressure and communicating said outlet of said first stage to the outlet of said distribution unit; and a second valve stage responsive to ambient pressure, located on an oxygen path between the outlet of said first stage and the outlet of said distribution unit, arranged for opening when said first predetermined altitude is exceeded.

* * * * *